United States Patent [19]

Dave et al.

[11] Patent Number: 5,269,180
[45] Date of Patent: Dec. 14, 1993

[54] BOREHOLE TOOL, PROCEDURES, AND INTERPRETATION FOR MAKING PERMEABILITY MEASUREMENTS OF SUBSURFACE FORMATIONS

[75] Inventors: Yogesh S. Dave, Stamford; T. S. Ramakrishnan, Bethel, both of Conn.

[73] Assignee: Schlumberger Technology Corp., New York, N.Y.

[21] Appl. No.: 761,213

[22] Filed: Sep. 17, 1991

[51] Int. Cl.$^5$ .................. E21B 49/00; G01N 15/08
[52] U.S. Cl. .................................. 73/152; 73/38; 73/155; 166/250
[58] Field of Search ............... 73/151, 152, 153, 155, 73/38; 166/250

[56] References Cited

U.S. PATENT DOCUMENTS

| | | | |
|---|---|---|---|
| 2,747,401 | 5/1956 | Doll | 73/151 |
| 3,209,588 | 10/1965 | Terry | 73/152 |
| 3,318,381 | 5/1967 | Brandt | 166/250 |
| 3,780,575 | 12/1973 | Urbanosky | 73/152 |
| 3,934,468 | 1/1976 | Brieger | 73/155 |
| 3,952,588 | 4/1976 | Whitten | 73/155 |
| 4,506,542 | 3/1985 | Rose | 73/38 |
| 4,507,957 | 4/1985 | Montgomery et al. | 73/151 |
| 4,513,612 | 4/1985 | Shalek | 73/155 |
| 4,543,821 | 10/1985 | Davis | 73/38 |
| 4,622,643 | 11/1986 | Dotson | 73/38 |
| 4,638,447 | 1/1987 | Odeh | 73/38 |
| 4,676,096 | 6/1987 | Bardsley et al. | 73/155 |
| 4,742,459 | 5/1988 | Lasseter | 364/422 |
| 4,860,581 | 8/1989 | Zimmerman | 73/155 |
| 5,065,619 | 11/1991 | Myska | 73/152 |

*Primary Examiner*—Tom Noland
*Assistant Examiner*—George Dombroske
*Attorney, Agent, or Firm*—David P. Gordon; Marc D. Foodman; Leonard W. Pojunas

[57] ABSTRACT

A borehole tool has a source probe in fluid contact with the borehole wall, a fluid flow line for bringing fluids to and from the source probe, two injection fluid chambers containing clean oil and clean water and in fluid contact with the fluid flow line, at least one sample chamber for receiving fluid from the formation, valves for selectively routing the formation fluids and the clean oil and water through the fluid flow line, at least one pressure controller for controlling whether fluid is to be injected or withdrawn from the formation via the source probe, and a pressure gauge for measuring the pressure seen at the source probe. Permeability measurements are made by sequentially injecting one clean fluid into the formation, followed by a cleaning of the line with the other fluid which was not injected, followed by the injection of the other fluid into the formation. The order in which the oil and water are injected is based on the type of mud used for drilling. Using the sequential injection preceded and separated by cleaning, end point effective and relative permeability determinations are made by measuring the pressure seen at the probe during steady-state injection conditions of known flow rate in order to calculate mobility of the fluid phase being injected; the mobility being related to the end point effective permeability via the viscosity of the liquid being injected.

32 Claims, 8 Drawing Sheets

BOREHOLE TOOL, PROCEDURES, AND INTERPRETATION FOR MAKING PERMEABILITY MEASUREMENTS OF SUBSURFACE FORMATIONS

BACKGROUND

1. Field of the Invention

This invention relates broadly to methods for investigating subsurface earth formations. More particularly, this invention relates to borehole tools and methods for determining the permeability and other hydraulic properties of earth formations surrounding boreholes.

2. State of the Art

The determination of permeability and other hydraulic properties of formations surrounding boreholes is very useful in gauging the producibility of formations, and in obtaining an overall understanding of the structure of the formations. For the reservoir engineer, permeability is generally considered a fundamental reservoir parameter, the determination of which is at least equal in importance with the determination of porosity, fluid saturations, and formation pressure. When obtainable, cores of the formation provide important data concerning permeability. However, cores are difficult and expensive to obtain, and core analysis is time consuming and provides information about very small sample areas. In addition, cores, when brought to the surface may not adequately represent downhole conditions. Thus, in situ determinations of permeability which can quickly provide determinations of permeabilities over larger portions of the formation are highly desirable.

The primary technique presently used for in situ determination of permeability is the "drawdown" method where a probe of a formation testing tool is placed against the borehole wall, and the pressure inside the tool (e.g., at a chamber) is brought below the pressure of the formation, thereby inducing fluids to flow into the formation testing tool. By measuring pressures and/or fluid flow rates at and/or away from the probe, and processing those measurements, determinations regarding permeability are obtained. These determinations, however, have typically been subject to large errors. Among the reasons for error include the fact that liberation of gas during drawdown provides anamolous pressure and fluid flow rate readings, and the fact that the properties of the fluid being drawn into the borehole tool are not known accurately. Another source of error is the damage to the formation (i.e., pores can be clogged by migrating fines) which occurs when the fluid flow rate towards the probe is caused to be too large.

Another technique which has been disclosed (although not used) for making in situ permeability measurements is the injection of fluids into the formation. An early mention of the use of injection is found in U.S. Pat. No. 2,747,401 to Doll. Doll discusses a multi-probe tool, and proposes the injection of either oil or water into the formation while monitoring the pressures at the observation probe in order to determine permeability. Doll also discusses withdrawal of fluid from the formation. More recent patent disclosures of permeability testing tools include U.S. Pat. No. 4,742,459 to Lasseter, and U.S. Pat. No. 4,860,581 to Zimmerman et al.; both of which are assigned to the assignee hereof. While both patents recognize that fluid injection is a possibility, both patents primarily disclose apparatus which withdraw fluid from the formation. The Zimmerman et al. patent mentions that in the drawdown method, it is essential to limit the pressure reduction so as to prevent gas liberation. In order to prevent gas liberation, Zimmerman et al. propose a flow controller which regulates the rate of fluid flow into the tool.

While the tools of the art are somewhat successful in obtaining valuable permeability information, they are still subject to errors. Moreover, the prior art tools do not address the chacterization of multiphase flow in the formation (e.g., oil and water), and therefore are incapable of providing determinations of effective endpoint permeabilities and relative permeabilities.

SUMMARY OF THE INVENTION

It is therefore an object of the invention to provide a borehole tool which includes means for injecting both clean oil and clean water into a formation and for means for measuring resulting pressures from which permeability determinations can be made.

It is another object of the invention to provide a borehole tool for making permeability measurements, where the tool has means for injecting fluids into a formation through flow lines, means for pulling fluids from the formation into flow lines and chambers, and means for cleaning the flow lines.

It is a further object of the invention to provide methods for utilizing a borehole tool which can inject clean oil and clean water into a formation, wherein the order in which oil and water are injected into the formation is dependent on the type of mud in the borehole.

Another object of the invention is to provide a borehole tool and methods for utilizing the borehole tool from which end point relative permeability determinations can be made.

In accord with the objects of the invention, a borehole tool is provided and generally comprises a source probe which is in fluid contact with the borehole wall, a fluid flow line for bringing fluids to and from the source probe, at least two injection fluid chambers containing respectively clean oil and clean water, with the injection fluid chambers being in fluid contact with the fluid flow line, at least one sample chamber for receiving fluid from the formation, a plurality of valves for selectively routing the formation fluids and the clean oil and water through the fluid flow line, at least one pressure control means for controlling whether fluid is to be injected or withdrawn from the formation via the source probe, and a pressure gauge for measuring the pressure seen at the source probe. If desired, the borehole tool can utilize additional probes, with the additional probes capable of measuring pressure and/or capable of fluid injection into the formation and fluid withdrawal from the formation. If the additional probes can inject and withdraw fluid from the formation, it is preferable to provide a flushing capacity for the flow lines coupled to the additional probes.

Another aspect of the borehole tool involves the configuration of the source probe. Preferably, the source probe has a conduit wall which is sufficiently rigid such that the internal diameter is not altered when in contact with forced up against the formation, while at the same time having an elastomeric forward section in order to permit a good seal with the borehole wall. In order to accomplish both requirements, the probe is made of metal with a tapered forward end around which of is molded an elastomeric substance. The probe is arranged to extend through a rubber packer.

With the provided borehole tool, the preferred method for making permeability measurements comprises sequentially injecting one of the clean oil and the clean water into the formation, followed by a flushing of the line with the other fluid which was not injected, followed by the injection of the other fluid into the formation. The order in which the oil and water are injected is based on the type of mud used for drilling and circulation, such that where an oil-based mud is used the clean oil is injected first followed by the clean water, and where a water-based mud is used, the clean water is injected first followed by the clean oil. Before the first injection of the clean oil or clean water, the fluid flow lines between the fluid source chamber and the source probe are preferably cleaned with the liquid to be injected so as to remove any contaminates such as borehole mud, mudcake, or formation fluids which might have entered the flow lines, e.g., during a drawdown procedure.

Using the sequential injection of clean water and clean oil preceded and separated by cleaning, end point effective permeability determinations and therefore endpoint relative permeability determinations can be made. The determinations are made by measuring the pressure seen at the probe (of known diameter) during steady-state injection conditions of known flow rate in order to calculate mobility of the fluid phase being injected; the mobility being related to the end point effective permeability via the viscosity of the liquid being injected.

As the provided borehole tool incorporates many of the details of the prior art, conventional drawdown procedures as well as other measurement procedures during formation fluid withdrawal can be used in conjunction with the interpretation methods available to provide additional determinations of permeability. It is also noted that because fluid injection simply involves a change of sign at the source (i.e., fluid flow in the opposite direction), fluid injection can be used in conjunction with already available interpretation methods.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
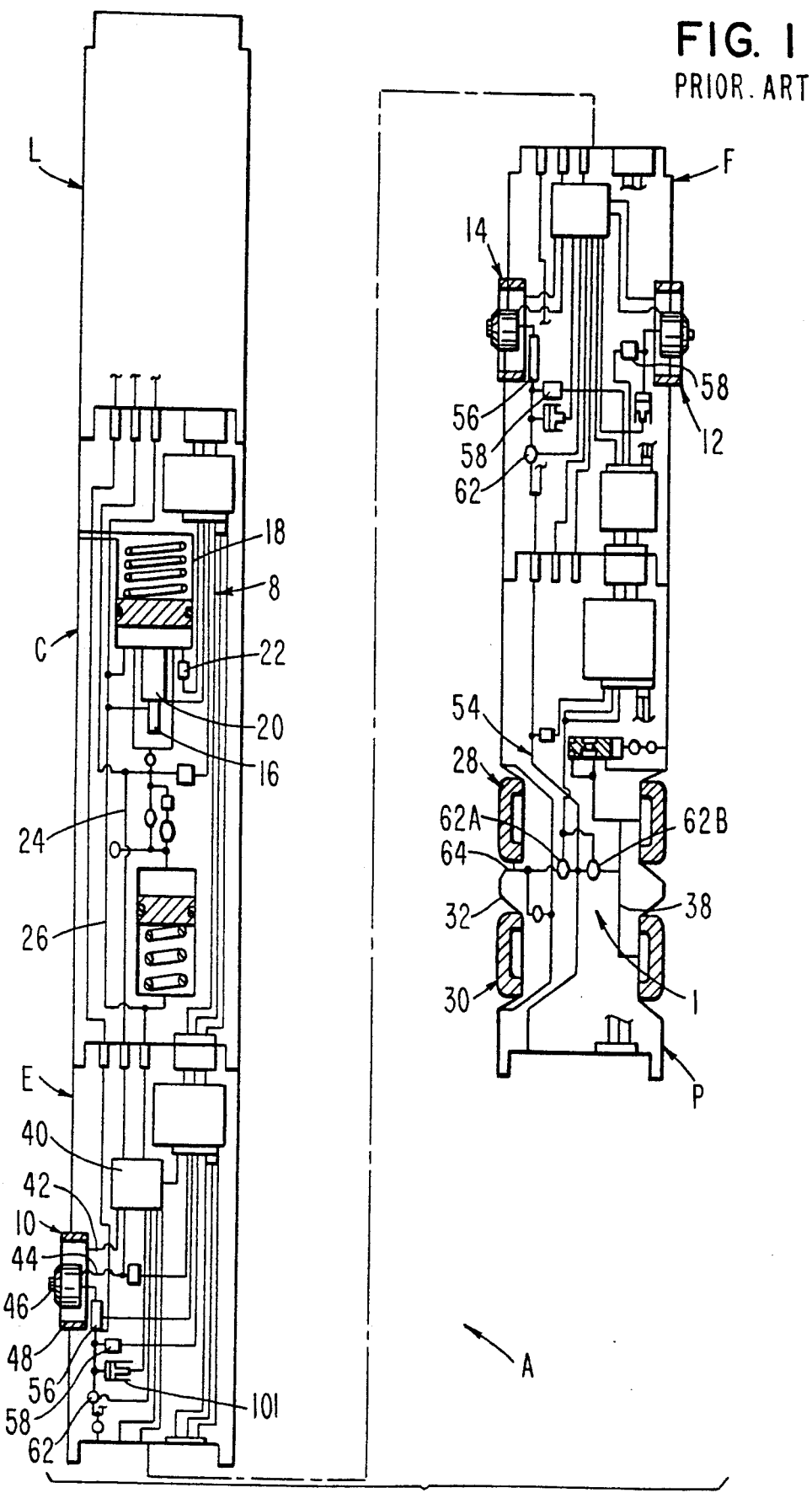
FIG. 1 is a schematic representation of a prior art apparatus which utilize modular components, most of which is preferably utilized as part of the apparatus of the invention.
Figure 2:
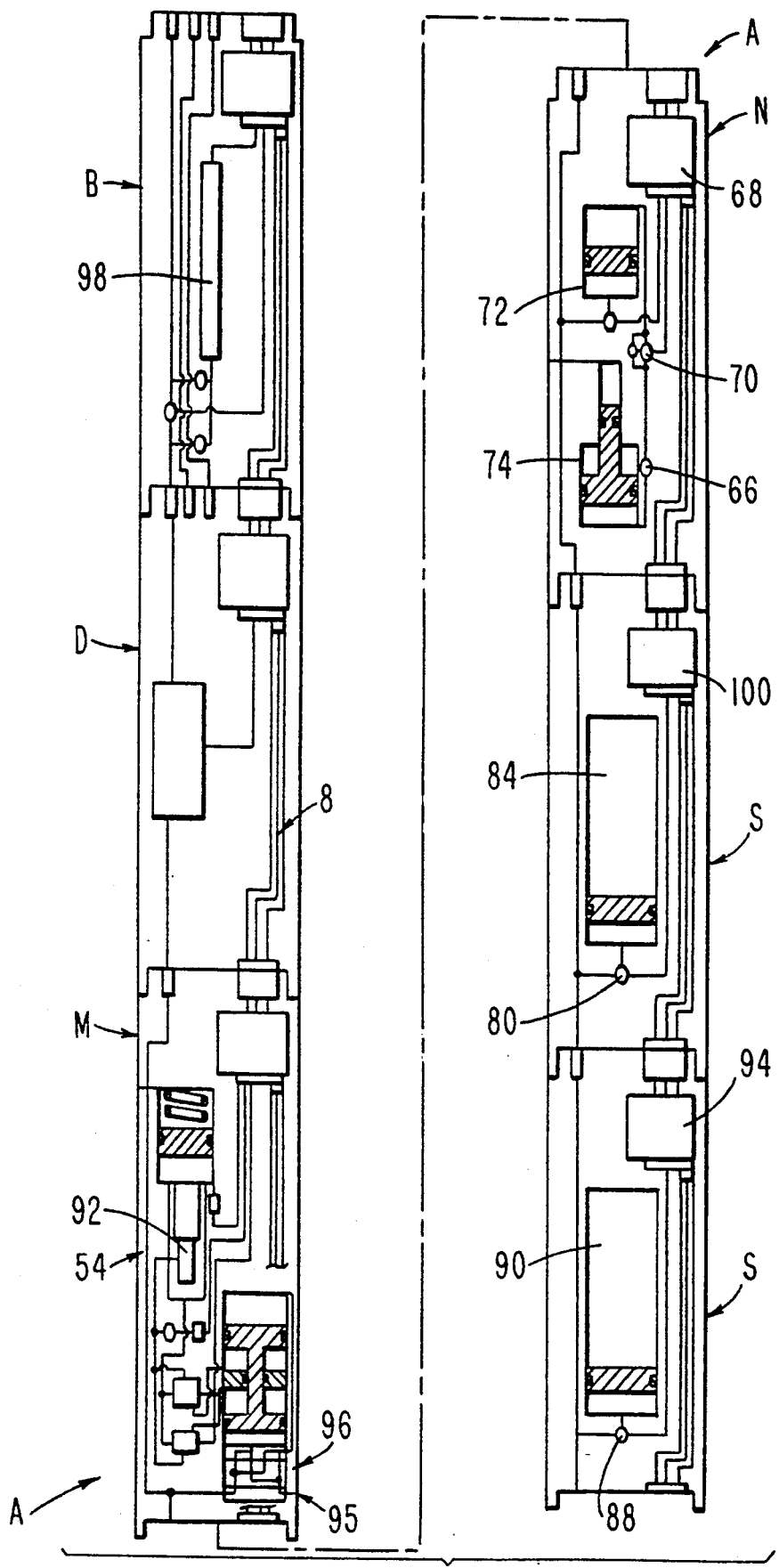
FIG. 2 is a schematic representation of additional modules of the prior art apparatus, most of which is preferably utilized as part of the apparatus of the invention.

Turning first to prior art FIGS. 1 and 2, details of a good portion of the preferred apparatus of the invention are seen. The apparatus A of FIGS. 1 and 2 is preferably of modular construction although a unitary tool is within the scope of the invention. The apparatus A is a down hole tool which can be lowered into the well bore (not shown) by a wire line (not shown) for the purpose of conducting formation property tests. The wire line connections to the tool as well as power supply and communications related electronics are not illustrated for the purpose of clarity. The power and communication lines which extend throughout the length of the tool are generally shown as numeral 8. These power supply and communication components are known to those skilled in the art and have been in commercial use in the past. This type of control equipment would normally be installed at the uppermost end of the tool adjacent the wire line connection to the tool with electrical lines running through the tool to the various components.

As shown in FIG. 1, the apparatus A has a hydraulic power module C, a packer module P, and a probe module E. Probe module E is shown with one probe assembly 10 which is used for permeability tests. When using the tool to determine anisotropic permeability and the vertical reservoir structure according to prior art techniques, a multiprobe module F can be added to probe module E. Multiprobe module F has a horizontal probe assembly 12 and a sink probe assembly 14.

The hydrualic power module C includes a pump 16, reservoir 18, and a motor 20 to control the operation of the pump. A low oil switch 22 also forms part of the control system and is used in regulating the operation of pump 16. It should be noted that the operation of the pump can be controlled by pneumatic or hydraulic means.

A hydraulic fluid line 24 is connected to the discharge of pump 16 and runs through hydraulic power module C and into adjacent modules for use as a hydraulic power source. In the embodiment shown in FIG. 1, hydraulic fluid return line 24 extends through hydraulic power module C into packer module P and probe module E or F depending upon which one is used. The loop is closed by virtue of hydraulic fluid line 26, which in FIG. 1 extends from probe module E back to hydraulic power module C where it terminates at reservoir 18.

The pump out module M can be used to dispose of unwanted samples by virtue of pumping the flow line 54 into the borehole or may be used to pump fluids from the borehole into the flow line 54 to inflate straddle packers 28 and 30. Pump 92 can be aligned to draw from flow line 54 and dispose of the unwanted sample through flow line 95, as shown on FIG. 2, or may be aligned to pump fluid from the borehole (via flow line 95) to flow line 54. The pump out module M has the necessary control devices to regulate pump 92 and align fluid line 54 with fluid line 95 to accomplish the pump out procedure. It should be noted that samples stored in sample chamber modules S can also be pumped out of the apparatus A using pump out module M. The pump out module M may also be used to accomplish constant pressure or constant rate injection if necessary. With sufficient power, the pump out module may be used to inject at high enough rates so as to enable creation of microfractures for stress measurement of the formation.

Alternatively, straddle packers 28 and 30 can be inflated and deflated with hydraulic fluid from pump 16. As can be readily seen, selective actuation of the pump out module M to activate pump 92 combined with selective operation of control valve 96 and inflation and deflation means I, can result in selective inflation or deflation of packers 28 and 30. Packers 28 and 30 are mounted to the outer periphery 32 of the apparatus A. The packers 28 and 30 are preferably constructed of a resilient material compatible with wellbore fluids and temperatures. The packers 28 and 30 have a cavity therein. When pump 92 is operational and inflation means I are properly set, fluid from flow line 54 passes through inflation/deflation means I, and through flow line 38 to packers 28 and 30. It should be noted that packer module P is typically only used during drawdown as opposed to injection.

As also shown in FIG. 1, the probe module E has probe assembly 10 which is selectively movable with respect to the apparatus A. Movement of probe assembly 10 is initiated by virtue of the operation of probe actuator 40. The probe actuator 40 aligns flow lines 24 and 26 with flow lines 42 and 44. As seen in FIG. 1, the probe 46 is mounted to a frame 48. Frame 48 is movable with respect to the apparatus A and probe 46 is movable with respect to frame 48. These relative movements are initiated by controller 40 by directing fluid from flow lines 24 and 26 selectively into flow lines 42 and 44 with the result being that the frame 48 is initially outwardly displaced into contact with the borehole wall. The extension of frame 48 helps to steady the tool during use and brings probe 46 adjacent the borehole wall. Since the objective is to obtain an accurate reading of pressure in the formation, which pressure is reflected at the probe 46, it is desirable to further insert probe 46 through the built up mudcake and into contact with the formation. Thus, alignment of flow line 24 with flow line 44 results in relative displacement of probe 46 into the formation by virtue of relative motion with respect to frame 47. The operation of probes 12 and 14 is similar.

Permeability measurements can be made by a multiprobe module F lowering the apparatus A into the borehole and inflating packers 28 and 30. It should be noted that such measurements can be accomplished using the probe modules E or E and F without packer module P. The probe 46 is then set into the formation as described above. It should be noted that a similar procedure is followed when using multiprobe module F and probe module E which contain vertical probe 46 and horizontal probe 12 and sink probe 14.

Having inflated packers 28 and 30 and/or set probe 46 and/or probes 46, 12 and 14, the fluid withdrawal testing of the formation can begin. As will be discussed with reference to FIGS. 3, 4a, and 4b, in the preferred embodiment of the invention, testing includes fluid injection through the probe 46 as well as formation fluid withdrawal. However, with respect to the prior art tool of FIGS. 1 and 2, a sample flow line 54 extends from the outer periphery 32 at a point between packers 28 and 30, through adjacent modules and into the sample modules S. Vertical probe 46 and sink probe 14 allow entry of formation fluids into the sample flow line 54 via a resistivity measurement cell 56, a pressure measurement device, and a pretest mechanism. Horizontal probe 12 allows entry of formation fluids into the pressure measurement device and pretest mechanism. When using module E or E and F, isolation valve 62 is mounted downstream of resistivity sensor 56. In the closed position, isolation valve 62 limits the internal flow line volume, improving the accuracy of dynamic measurements made by pressure gauge 58. After initial pressure tests are made, isolation valve 62 can be opened to allow flow into other modules. When taking initial samples, there is a high prospect that the first fluid obtained is contaminated with mud cake and filtrate. It is desirable to purge such contaminants from the sample to be taken. Accordingly, the pumpout module M is used to initially purge from the apparatus A specimens of formation fluid taken through inlet 64 or vertical probe 46 or sink probe 14 to flow line 54. After having flushed out the contaminents from the apparatus A, formation fluid can continue to flow through sample flow line 54 which extends through adjacent modules such as precision pressure module B, fluid analysis module L, pump out module M (FIG. 2), flow control module N and any number of sample chamber modules S which may be attached. By having a sample flow line 54 running the longitudinal length of various modules, multiple sample chamber modules S can be stacked without necessarily increasing the overall diameter of the tool. The tool can therefore take more samples before having to be pulled to the surface and can be used in smaller bores.

If desired, a multisample module for storing clean fluids for injection, or for sampling formation fluids can be used in the borehole tool string.

The flow control module N includes a flow sensor 66, a flow controller 68 and a selectively adjustable restriction device such as a valve 70. A predetermined sample size can be obtained at a specific flow rate by use of the equipment described above in conjunction with reservoirs 72 and 74. Having obtained a sample, sample chamber module S can be employed to store the sample taken in flow control module N. To accomplish this, a valve 80 is opened and valves 62, 62A and 62B are held closed, thus directing the sample just taken into a chamber 84 in sample chamber module S. The tool can then be moved to a different location and the process repeated. Additional samples taken can be stored in any number of additional sample chamber modules S which may be attached by suitable alignment of valves. For example, as shown in FIG. 2, there are two sample chambers S illustrated. After having filled the upper chamber by operation of valve 80, the next sample can be stored in the lowermost sample chamber module S by virtue of opening valve 88 connected to chamber 90. It should be noted that each sample chamber module has its own control assembly, shown in FIG. 2 as 100 and 94. Any number of sample chamber modules S or no sample chamber modules can be used in particular configuration of the tool depending upon the nature of the test to be conducted.

As shown in FIG. 2, sample flow line 54 also extends through a precision pressure module B and a fluid analysis module D. The gauge 98 should preferably be mounted as close to probes 12, 14 or 46 to reduce internal piping which, due to fluid compressibility, may affect pressure measurement responsiveness. The precision gauge 98 is more sensitive than the strain gauge 58 for more accurate pressure measurements with respect to time. Gauge 98 can be a quartz pressure gauge which has higher static accuracy or resolution than a strain gauge pressure transducer. Suitable valving and control mechanisms can also be employed to stagger the operation of gauge 98 and gauge 58 to take advantage of their difference in sensitivities and abilities to tolerate pressure differentials.

Various configurations of the apparatus A can be employed depending upon the objective to be accomplished. For basic sampling, the hydraulic power module C can be used in combination with the electric power module L, probe module E and multiple sample chamber modules S. For reservoir pressure determination, the hydraulic power module C can be used with the electric power module L, probe module E and precision pressure module B. For uncontaminated sampling at reservoir conditions, hydraulic power module C can be used with the electric power module D, probe module E in conjunction with fluid analysis module L, pump out module M and multiple sample chamber modules S. To measure permeability, the hydraulic power module C can be used in combination with the electric power module L, probe module E, precision pressure module B, flow control module N and multiple sample chamber modules S. For good anisotropy measurements, the hydraulic power module C can be used with probe module E, multiprobe module F, the electric power module L, precision pressure module B, flow control module N and multiple sample chamber modules S. A simulated Drill Stem Test (DST) test can be run by combining the electric power module L with packer module P, and precision pressure module B and sample chamber modules S. Other configurations are also possible and the makeup of such configurations also depends upon the objectives to be accomplished with the tool. The tool can be of unitary construction as well as modular; however, the modular construction allows greater flexibility and lower cost, to users not requiring all attributes.

The individual modules may be constructed so that they quickly connect to each other. Preferably, flush connections between the modules are used in lieu of male/female connections to avoid points where contaminants, common in a wellsite environment, may be trapped.

It should also be noted that the flow control module is also adapted to control the pressure while a sample is being taken.

Use of particular packer module P allows a sample to be taken through inlet 64 by drawing formation fluid from a section of the well bore located between packers 28 and 30. This increased well bore surface area permits greater flow rates to be used without risk of drawing down the sample pressure to the bubble point of the formation fluid thus creating undesirable gas which affects the permeability test results.

Additionally, as described earlier, the use of the apparatus A permits the use of multiple probes at a distance far greater than the few centimeters disclosed in U.S. Pat. No. 2,747,401. In order to determine formation permeability unaffected by drilling damage and formation invasion, with a measurable pressure response, adequate probe spacing in the neighborhood of one to three feet is preferred.

Flow control of the sample allows different flow rates to be used. Flow control is useful in getting meaningful formation fluid samples as quickly as possible to minimize the chance of binding the wireline and/or the tool because of mud oozing onto the formation in high permeability situations. In low permeability situations, flow control is helpful to prevent drawing formation fluid sample pressure below its bubble point.

In sum, with reference to the prior art FIGS. 1 and 2, the hydraulic power module C provides the basic hydraulic power to the apparatus A. In view of the hostile conditions which are encountered downhole, a brushless DC motor may be used to power pump 16. The brushless motor may be encased in a fluid medium and include a detector for use in switching the field of the motor. The probe module E and multiprobe module F include a resistivity measurement device 56 which distinguishes, in water based muds, between filtrate and formation fluid when the fluid analysis module L is not included in the apparatus A. The valve 62 minimizes the after flow when performing permeability determinations. The fluid analysis module D is designed to discriminate between oil, gas and water. By virtue of its ability to detect gas the fluid analysis module D can also be used in conjunction with the pump out module M to determine formation bubble point. The flow control module N further includes a means of detecting piston position which is useful in low permeability zones where flow rate may be insufficient to completely fill the module. The flow rate may be so low it may be difficult to measure; thus, detection of piston position allows a known volumetric quantity to be sampled.

Figure 3:
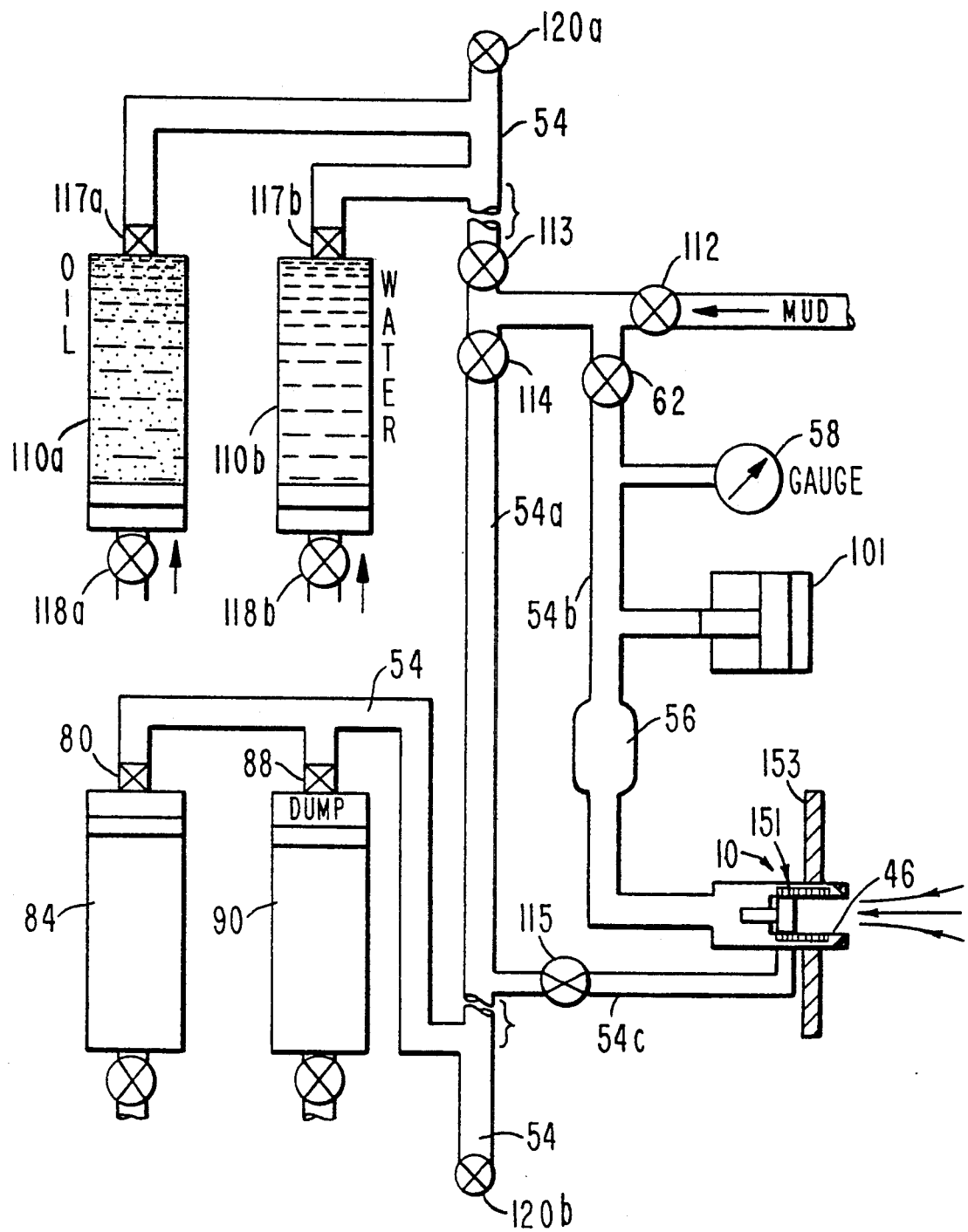
FIG. 3 is a schematic representation of the fluid chambers, flowlines, and valves of the apparatus of the invention.

Turning to FIG. 3, a schematic diagram of the improvement to the prior art tool of FIGS. 1 and 2 is seen. Because many of the components shown in FIG. 3 are exactly what was already shown in FIGS. 1 and 2, it will be immediately apparent to those skilled in the art as to how to accommodate the additional aspects of FIG. 3 into the tool of FIGS. 1 and 2. In particular, the flow line 54, probe assembly 10 and probe 46, resistivity cell 56, pressure gauge 58, isolation valve 62, pretest expansion chamber 101, and formation sample chambers 84 and 90 and their associated valves 80 and 88, as shown in FIG. 3 are intended to correspond to what is shown in FIGS. 1 and 2, although the relative vertical locations of the probe 46, the resistivity cell 56, pretest expansion chamber 101, pressure gauge 58, and isolation valve 62 are preferably reversed. The additional fluid flow components of the invention include the clean oil injection sample chamber 110a and associated valves 117a and 118a, the clean water injection sample chamber 110b and associated valves 117b and 118b, equalizing valve 112 (which is known in the art), bypass valves 113, 114, and 115, module valves 120a and 120b, and flowline branches 54a, 54b, and 54c. Although not shown, additional clean fluid sample chambers can be provided, if desired.

In the preferred embodiment, the clean oil and clean water injection sample chambers 110a and 110b are respectively filled with clean oil and clean water samples of known viscosities, and are preferably located in the borehole tool above the isolation valve 62, pressure gauge 58, pretest chamber 101, and probe 46. Associated seal valves 117a and 117b, which may be driven hydraulically or electrically, are used to permit flow of oil and water out of the respective sample chambers and into flow line 54. The clean oil and clean water are used for flushing the flow line 54, and for injection into the formation, both of which will be described in more detail hereinafter.

Equalizing valve 112, which sits between a line open to borehole pressure and flow line 54, equalizes the differential pressure between the flow line 54 and the borehole while the tool is being run in the borehole. In the prior art, equalizing valve 112 is normally kept open during movement of the tool in the borehole. However, in accord with the hereinafter described preferred method invention, it might be preferable to keep the equalizing valve 112 closed and the filter valve (which is part of the probe device 46) sealed in order to eliminate the flow of borehole mud into flow line 54. In order to keep equalizing valve 112 closed during borehole travel, a separate pressure compensator and valve mechanism must be provided. In fact, sample chambers 110a and 110b which are arranged as pistons can act as pressure compensators as long as they are provided with valves 118a and 118b which can be opened to the borehole mud. When valves 117a and 118a, or 117b and 118b are open, the pressure of the borehole acts on the respective chamber which in turn pressurizes flow line 54.

Isolation valve 62 isolates different sections 54a and 54b of the flow line 54 during different measurement sequences. It is also used to isolate lines 54a and 54b during the hereinafter described cleaning operation. The valve is preferably closed during pretest withdrawal or injection, thus isolating the rest of the tool flow line from the probe-pretest section.

Additional isolation valves 113, 114, and 115, which are also called bypass valves, are provided to isolate various sections of flow line 54. In particular, with isolation valves 62 and 115 closed, line 54b is completely isolated from line 54a. Such an arrangement may be desirable during a drawdown pretest. Such an arrangement is also provided in conjunction with open valves 113 and 114 when it is desirable to clean line 54a. On the other hand, where it is desirable to clean line 54b, isolation valve 114 can be closed with valves 113, 62, and 115 open. With this arrangement, fluid will flow through line 54 and valve 113, down through valve 62 and line 54b to probe 46 (with the filter valve preferably closed), and out through line 54c and valve 115. If valve 120b is closed and the valve 80 or 88 to one of sample or dump chambers 84 or 90 open, the fluid or material previously contained in line 54b and 54c will be dumped into the sample or dump chamber.

Because line 54c is preferably a small line which is coupled to the front of the probe 46 (which itself is of small diameter), when a sample is being taken from the formation for storage in chamber 84 or 90, bypass valve 115 and isolation valve 113 are closed, and isolation valves 62 and 114 are open. This permits a fluid sample which is taken from the formation to flow first through line 54b and then through line 54a. Alternatively, for fluid flow at low flow rates, bypass valve 115 can be opened and isolation valves 62 and 114 closed.

It will be appreciated by those skilled in the art that valve 113 effectively separates a domain of clean fluids from a domain of contaminated fluids. Similarly, while breaks in line 54 are intended to show separation of modules, valves 120a and 120b effectively isolate the beginning or end of the modules so as to force fluids in the desired directions.

Figure 4:
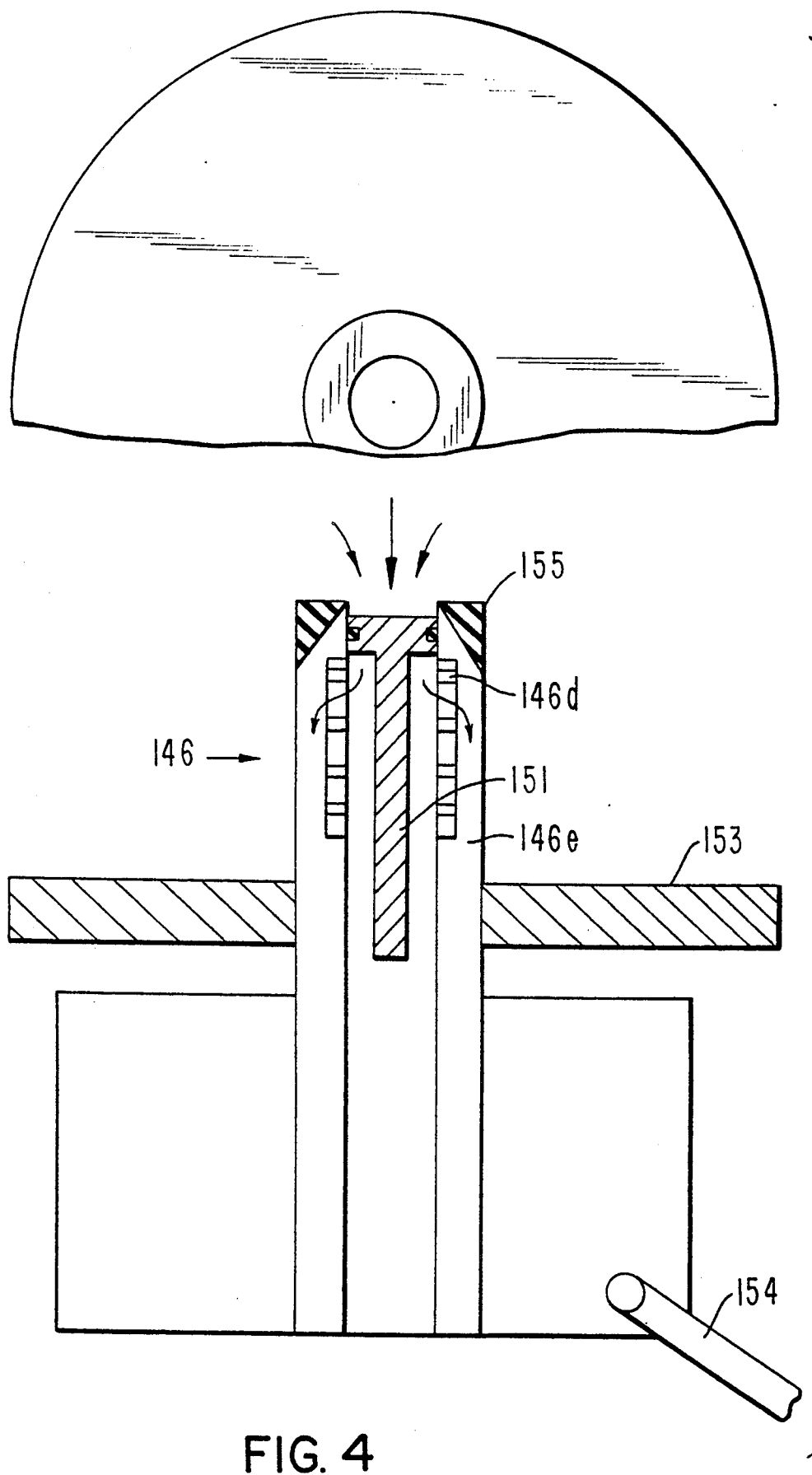
FIG. 4 is a expanded schematic view of the preferred probe of the invention.

Before turning to the method invention which utilizes the flow apparatus shown in FIG. 3, in accord with another aspect of the invention, an improved probe 146 is provided for the apparatus as seen in FIG. 4. The improved probe 146 comprises a piston 151 made of metal which extends through a packer 153, with the piston having a small radius tube 154 which extends therethrough. As shown in FIG. 4, the outer diameter of the forward portion of piston 151 (i.e., that portion which is intended to be closest to contacting the formation) tapers in thickness until it comes almost to a point. The decrease in metal thickness is compensated with an elastomer 155 which increases in thickness as the piston wall descreases in thickness. With the provided improved probe 146, the rigidity of the internal diameter of the probe is maintained when the probe is in contact with the formation, while a good fluid seal is provided by the elastomer 155.

Figure 5A:
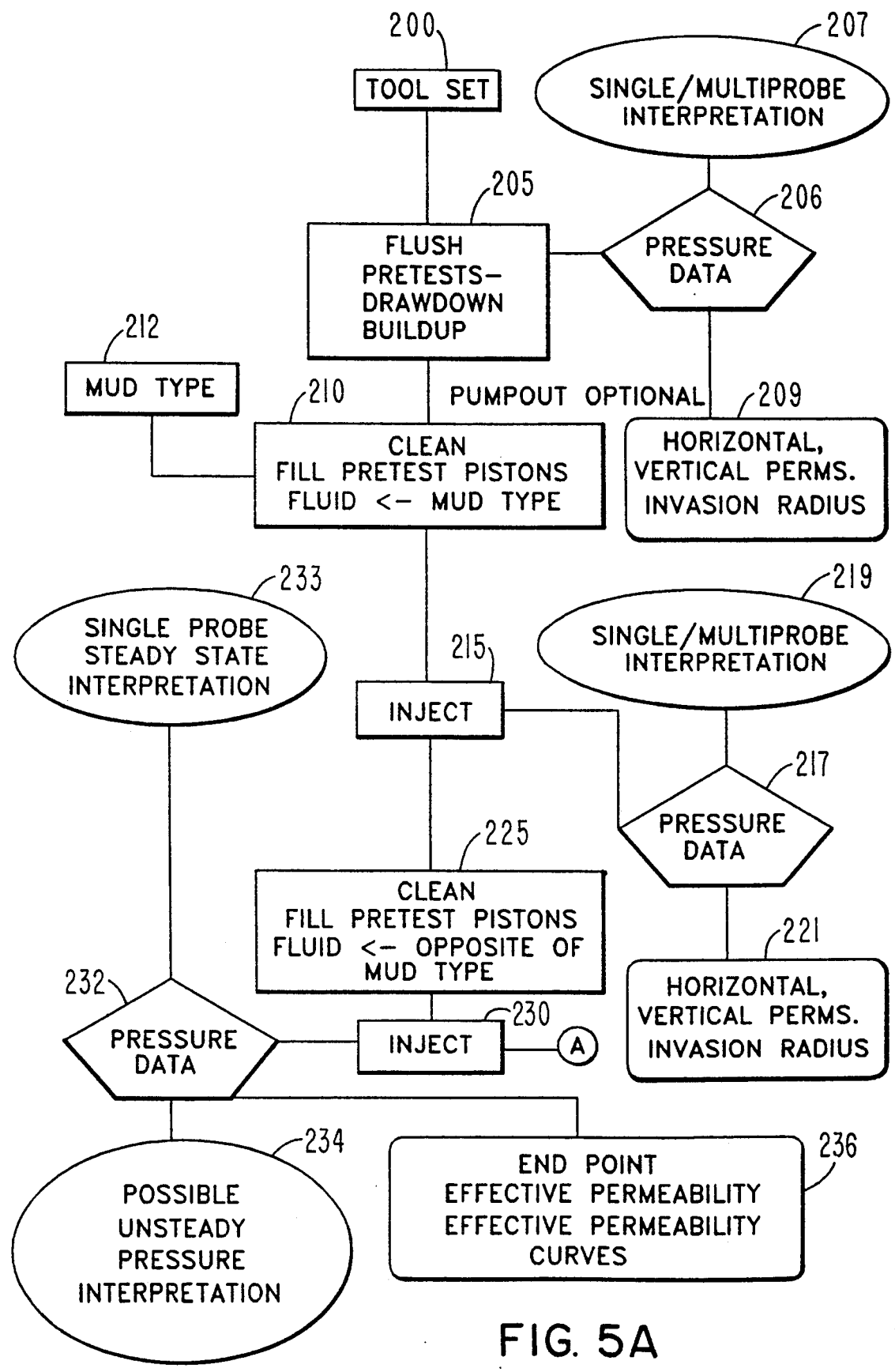
FIGS. 5a and 5b are flow charts which together comprise the preferred method of the invention for making permeability measurements.
Figure 5B:
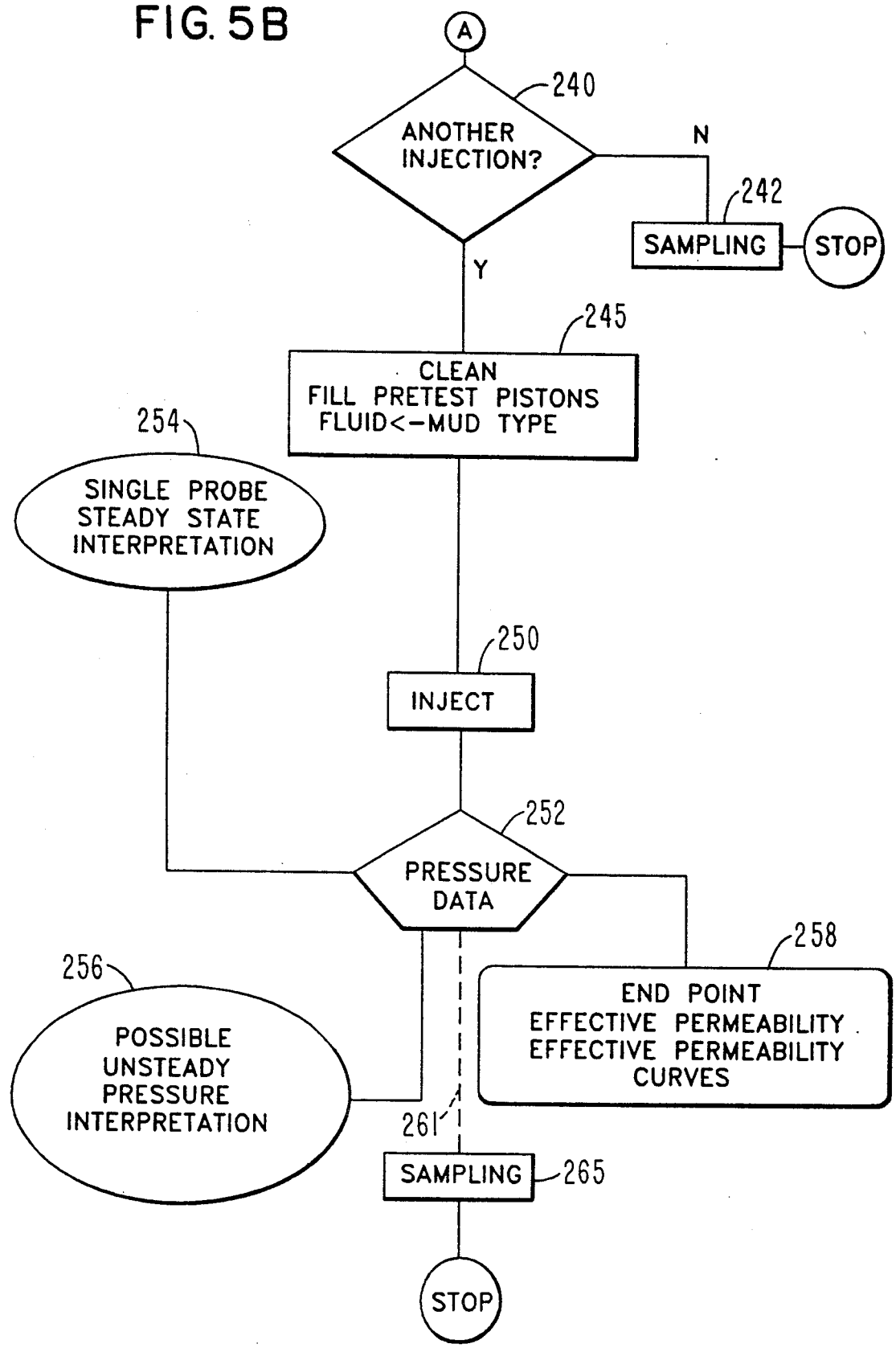

Turning to FIGS. 5a and 5b, the preferred method of the invention is shown in flow diagram format. In order to make measurements, the borehole tool must be set at 200 so that communication with the formation is established. In setting the tool, the packer 153 around the probe provides a seal that prevents the mud column from communicating with the tool. The filter valve which is comprised by the piston 151 and the slits 146d in a cylinder 146e of the probe 146 is opened while the equalizing valve 112, bypass valve 115, and isolating valve 62 are kept closed. This permits the probe (i.e., the gauge 58) to measure reservoir pressure while flushing the mudcake out from between the probe and formation. The mudcake between the probe and formation is further removed at the pretest or drawdown step 205 such that any loose particles blocking the probe are cleared. If a pretest is to be done at step 205, the isolation valve 62 is kept closed while the mudcake and some formation fluid is drawn into pretest chamber 101. If flushing by drawdown is to be done at step 205, valves 62 and 114 are kept open, while valve 113 is closed, and the valve 88 to the dump chamber 90 is opened for a short time. If desired, both pretest and sampling may be accomplished at step 205 (sampling requiring that a valve to a sample chamber, e.g., valve 80 to chamber 84, be kept open). It will be appreciated that both procedures are well known in the art. The information shown at 206 obtained during pretest can be used in a single or multiprobe interpretation as indicated at step 207, and/or can be used to provide horizontal and vertical permeability information, as well as invasion radius information as indicated at step 209.

At step 210, a cleaning operation is undertaken. The cleaning operation is provided to prevent solids plugging the formation during fluid injection, which plugging would affect the permeability measurement. In cleaning, the pretest piston is preferably filled with the fluid to be injected first into the formation while the tool remains set. At the same time, the filter valve should remain shut to prevent communication with the formation. To do this, the set and retract lines (of FIGS. 1 and 2) are pressured simultaneously. Since the contact area of the filter valve piston is smaller on the set-line connnection, the filter valve should close. Similarly, the piston area for the setting piston is larger on the set side than on the retract side. Therefore, the tool remains set as well. The cleaning of flow lines is performed at step 210 by driving the clean fluid from the sample chamber 110 through lines 54a, 54b, and 54c. This may be done in several ways. A preferred manner is to first open valves 113 and 114, While keeping valves 62 and 115 closed. Then clean fluid from one of chambers 110a and 110b is forced through line 54a and into dump chamber 90 or out into the borehole. Afterwards, valve 114 is closed, while valves 62 and 115 are opened. Clean fluid is then forced through lines 54b and 54c and out into dump chamber 90 or into the borehole. Once this procedure is completed, the pretest piston 101 is moved back and filled with about 20 cc of clean fluid. This permits the pretest piston 101 rather than the pumpout module (see FIGS. 1 and 2) to then be used for the injection step. After the pretest piston is filled with clean fluid, the sample and dump chambers are closed by closing valaves 117 and 88. It should be noted that cleaning of line 54a is not necessary prior to fluid injection.

As previously mentioned, and as indicated in FIG. 5a, the type of clean fluid used to initially clean the lines depends upon which clean fluid is to be first injected into the formation. That decision is preferably made according to the type of mud used in the borehole, with the mud type input to step 210 being shown at 212. Where the mud is a water based mud, water is preferably injected first, followed by oil. Hence, the initial cleaning step 210 would use clean water. Where the mud is an oil based mud, however, oil is preferably injected first, followed by water. Hence, the initial cleaning step would use clean oil. It should be noted that where an oil based mud is used in an oil-wet formation, an additional step of injecting oil after the water injection may be desirable.

The injection sequence starts with the injection at 215 of fluid which is the same as the mud type. Typically, at least 10 cc, and preferably 20 cc of clean fluid is injected into the formation by pretest piston 101 under constant pressure (although constant pressure is not required). The rate of injection, which may be monitored by the piston travel, is preferably continuously monitored to give the corresponding flow rate of liquid into the formation. Based on the pressure(s) and flow rate(s) obtained at step 217, single and/or multiprobe interpretation may be carried out at 219, and horizontal and vertical permeabilities and invasion radius determined at step 221 according to prior art techniques; it being understood that the flow rate and/or measured pressures having the opposite sign than would occur with drawdown techniques.

Figure 6:
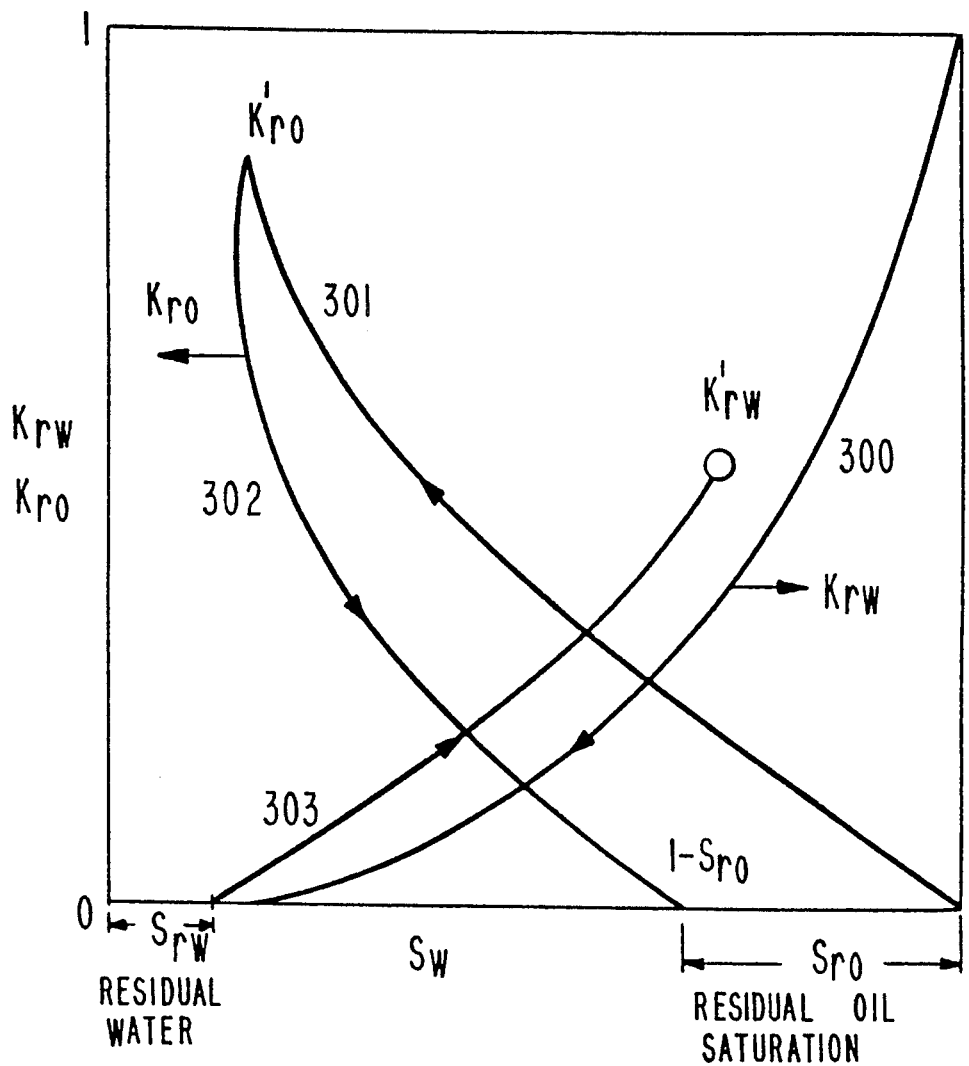
FIG. 6 is a graph of water saturation versus relative oil and water permeabilities which is useful in understanding endpoint relative permeabilities.

After the injection step of 215 is completed, the flow lines are cleaned at step 225 in much the same way described above with reference to step 210 except that the other clean liquid is used to clean the lines. Again, during the cleaning step, the pretest piston 101 is preferably filled with clean fluid (now of the second type), and at step 230, the clean fluid is injected into the formation. As with the other injection step, pressure data and/or fluid flow rates are gathered at step 232. This data may then be used as indicated at steps 233, 234, and 236 to conduct a single probe steady state interpretation, an unsteady state interpretation, and perhaps most importantly, an end point effective permeability determination which will be described more particularly with reference to FIGS. 6 and 7.

It will be appreciated that the injection of one clean liquid into the formation followed by the injection of the second clean liquid into the formation will not necessarily terminate the experiments accomplishable. Thus, as shown in FIG. 5b, if another injection is not desired at 240, sampling of the formation might be carried out at step 242 prior to moving the tool to a new location in the borehole. However, if additional injection information is desired, at step 245, another cleaning step is carried out (if required) prior to injection at step 250. During injection, pressure and/or flowrate data are obtained as indicated at 252, and additional interpretation and permeability determinations are made as indicated at 254, 256, and 258. As indicated by dashed line 261, the cleaning, injection, and data gathering can continue as desired. However, after the final injection, if desired, the formation may be sampled as indicated at step 265 prior to moving the tool to a new borehole location.

With the pressure and/or flowrate information obtained during the injection of clean oil and clean water into the formation, information regarding relative end point permeabilities can be obtained. It is well known in the art, that the velocity (v) of fluid moving through a sample is related to the permeability (k) of the sample, and the shear coefficient of viscosity (m) of the liquid according to Darcy's law:

$$v = (k/m)(P_1 - P_2)/l \qquad (1)$$

$(P_1 - P_2)$ is the pressure difference over the sample, and l is the length of the sample. The velocity may also be defined according to $$v = -L\nabla p \qquad (2)$$

where $L = k/m$ and is called mobility, while $\nabla p$ is the pressure gradient. In one dimensional, incompressible flow, equation (2) may be integrated to give equation (1).

Considering two phase flow (e.g., water and oil inside a rock), if the pore space of the rock is $V_p$, and the volume of water and oil are respectively $V_w$ and $V_o$, the water saturation may be defined by $S_w = V_w/V_p$, while the oil saturation is defined by $S_o = 1 - S_w$, or $1 - (V_w/V_p) = V_o/V_p$. If upstream and downstream pressures of both oil and water are defined as $P_{1o}$, $P_{2o}$, and $P_{1w}$, $P_{2w}$ and oil and water velocities $v_o$ and $v_w$ are measured, then $$v_o = L_{co}(P_{1o} - P_{2o})/l \qquad (3)$$

$$v_w = L_{cw}(P_{1w} - P_{2w})/l \qquad (4)$$

where $L_{co}$ and $L_{cw}$ are effective mobilities whch are functions of $S_w$ and are respectively equal to $k_{co}/m_o$ and $k_{cw}/m_w$. It has been found that when the water saturation is large, the effective mobility of the water is large while the effective mobility of the oil is small. The relatively small effective mobility of the oil is due both to reduced flow area as well as increased tortuosity.

Taking the ratio of the effective mobility of water in the sample to the mobility of water where the sample is completely saturated with water yields a relative water permeability; i.e., $$L_{cw}/L = k_{cw}/k = k_{rw} \qquad (5)$$

Similarly, taking the ratio of the effective mobility of oil in the sample to the mobility of oil where the sample is completely saturated with oil yields a relative oil permeability; i.e., $$L_{co}/L = k_{co}/k = k_{ro} \qquad (6)$$

In reality, there is always trapping of one phase by the other. Thus, if it were possible to start with a sample having a water saturation of one and to introduce oil into the sample, the water saturation would decrease but would never reach zero. In fact, as shown by curves 300 and 301 in FIG. 6, the water saturation of a typical rock sample under such circumstances would typically settle at between 0.1 and 0.3; i.e., the residual water saturation would be between 0.1 and 0.3. As the water saturation decreases, the oil saturation increases as indicated by curves 300 and 301. However, since the water saturation never reaches zero, the oil saturation never reaches one. Hence, an endpoint relative permeability to oil is defined at $k'_{ro}$, with $$k'_{co} = k'_{ro}k \quad (7)$$

and with $L'_{co} = k'_{co}/m_o$.

Now, if the same rock which has residual water saturation but is otherwise fully saturated with oil is subjected to a gradual reinjection of water, the oil saturation will decrease as indicated by curves 302 and 303 while the water saturation increases. However, the water saturation will not reach a value of one, but some other value equal to $1-S_{ro}$, where $S_{ro}$ is the residual oil saturation. As indicated, an endpoint relative permeability to water $k'_{rw}$ is reached at the point at the residual oil saturation point.

In practice, for a water based mud, water wet formation, when water seeps into the formation due to invasion, the formation sits at residual oil saturation. At this point oil is virtually trapped and only water moves. The water permeability then would be equal to $kk'_{rw}$ (where k is the single phase permeability). This is what would be measured by simply injecting clean water into the formation. When clean oil is then injected into the formation, the permeability $kk'_{ro}$ is measured.

Figure 7:
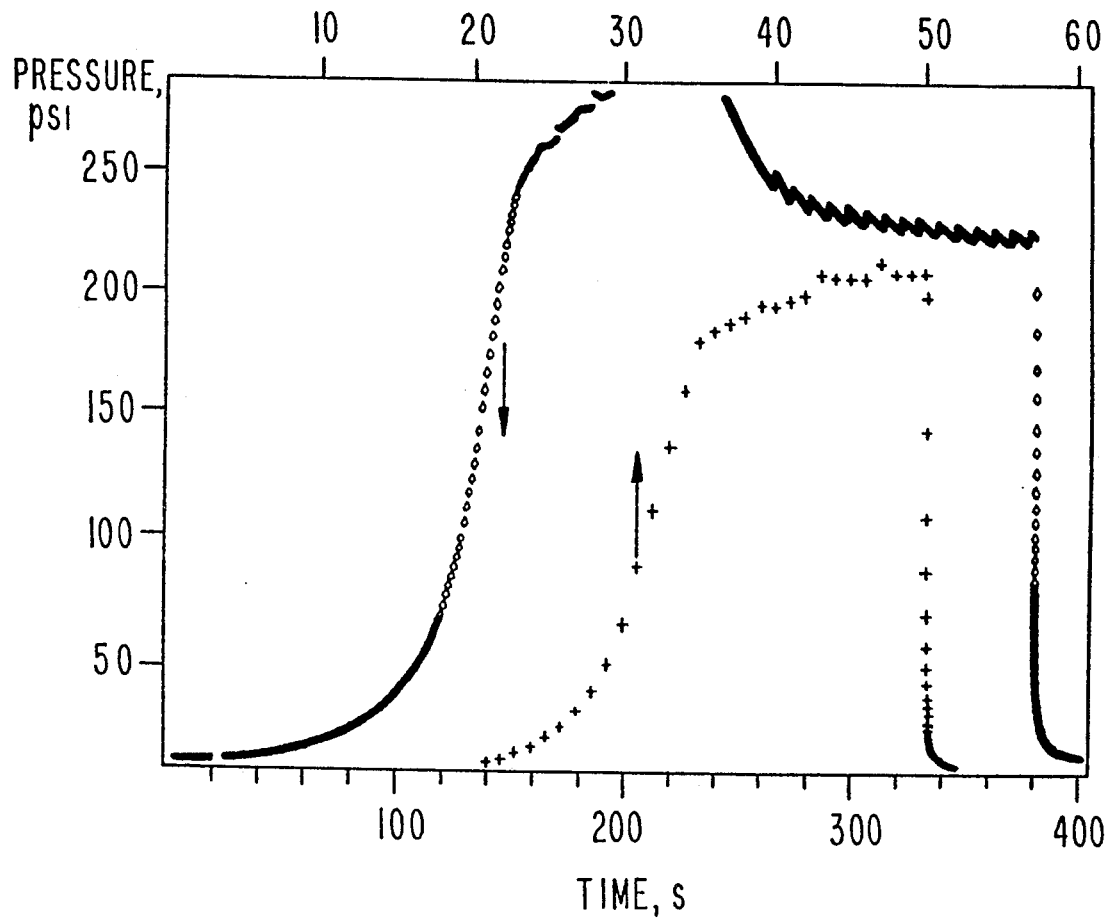
FIG. 7 is a graph showing measured test probe pressure versus time during oil injection and water injection into a synthetic formation.

An understanding of the physics which permits endpoint effective permeability determination from measurement of pressures taken during successive injections of clean water and oil (or oil and water) may be gained by recognizing that the source probe pressure is always sensitive to fluid properties close to the probe itself. This has to do with the nature of the flow which goes from near probe flow, to hemispherical and then spherical flow. Experimental laboratory evidence supports this understanding. In the experiment, water and oil were injected sequentially through a probe into a medium whose geometry was carefully chosen to mimic downhole flow geometry. Pressure measurements recorded are shown in FIG. 7. The steady state pressure during water injection was used to deduce the single phase permeability. The oil injection steady state pressure was likewise used to obtain the endpoint effective mobility of oil. After adjusting for viscosities, a value of $k'_{ro} = 0.70$ was calculated. Cores taken from the sample were subjected to careful linear flow endpoint effective permeability measurement, where a value of $k'_{ro} = 0.66$ was obtained. Thus, the probe measurement compares favorably to the core measurement and proves the feasibility of measuring endpoint effective permeabilities with a probe-like device. It can be seen from FIG. 7, that steady state was reached during water injection after the injection of approximately 5 cc of water, while steady state was reached during oil injection after the injection of about 15 cc of oil.

There has been described and illustrated herein borehole tools, procedures, and methods useful in making in situ permeability, and in particular in situ endpoint effective/relative permeability determinations in an open borehole. While particular embodiments of the invention have been described, it is not intended that the invention be limited thereto, as it is intended that the invention be as broad in scope as the art will allow and that the specification be read likewise. Thus, while a particular modular borehole tool was described, it will be appreciated that other borehole tools could be utilized provided that separate chambers for clean oil and clean water are provided, and means are provided for cleaning the lines. Also, while particular interpretations of the physics of injecting clean water after clean oil, and vice versa in the formation have been set forth, it will be appreciated that other interpretations, including prior art single phase interpretations can be used as desired. It will therefore be appreciated by those skilled in the art that yet other modifications could be made to the provided invention without deviating from its spirit and scope as so claimed.

We claim:

1. A borehole tool for use in an uncased borehole in a formation, comprising:
    a) a source probe means for making fluid contact with a wall of said borehole;
    b) a fluid flow line for bringing fluids to said source probe;
    c) at least one injection fluid chamber containing one of clean oil and clean water, with said injection fluid chamber being in fluid communication with said fluid flow line;
    d) pressure measurement means for measuring pressure resulting from the injection of said one of clear oil and clean water through said source probe means and into said formation; and
    e) cleaning means for cleaning said source probe means and at least a portion of said fluid flow line prior to the injection of said one of clean oil and clean water into said formation.

2. A borehole tool according to claim 1, further comprising:
    f) at least one pressure control means for controlling the injection of fluid in said flow line via said source probe into said formation.

3. A borehole tool according to claim 2, further comprising:
    g) at least one sample chamber for receiving fluid from said formation; and
    h) at least one valve for selectively routing said fluid received from said formation through said fluid flow line.

4. A borehole tool according to claim 1, wherein:
    said pressure measurement means comprises a pressure gauge for measuring the pressure seen at said source probe.

5. A borehole tool according to claim 4, wherein:
    said at least one pressure control means comprises a pretest piston means coupled to said fluid flow line.

6. A borehole tool according to claim 4, wherein:
    said at least one pressure control means comprises a pump means coupled to said fluid flow line.

7. A borehole tool according to claim 4, wherein:
    said at least one pressure control means comprises a plurality of second valve means coupled between respective ones of said at least two injection fluid chambers and said uncased borehole, wherein when a particular said second valve means is open, borehole mud pressure bears on a respective said injection fluid chamber.

8. A borehole tool according to claim 4, wherein:
    said at least one pressure control means also controls the withdrawal of fluid from said formation into said fluid flow line via said source probe.

9. A borehole tool according to claim 4, wherein:
    said fluid flow line comprises a first flow line branch coupled to said at least two injection fluid chambers and a second flow line branch coupled between said first flowline branch and said source probe.

10. A borehole tool according to claim 9, further comprising
an isolation valve between said first flow line branch and said second flow line branch.

11. A borehole tool according to claim 10, further comprising:
f) at least one sample chamber for receiving fluid from the formation, wherein
said sample chamber is coupled to said first flow line branch.

12. A borehole tool according to claim 9, wherein:
said source probe has a tip, and
said fluid flow line further comprises a third flow line branch coupled adjacent said tip of said source probe and coupled to said first flow line branch.

13. A borehole tool according to claim 12, further comprising a plurality of valves including first isolation valve between said first flow line branch and said second flow line branch, and a second isolation valve between said third flow line branch and said first flow line branch.

14. A borehole tool according to claim 13, wherein:
said first flow line branch is coupled to said second flow line branch at a first location,
said first flow line branch is coupled to said third flow line branch at a second location, and
said plurality of valves further includes a third isolation valve located along said first flow line branch between said first and second locations.

15. A borehole tool according to claim 12, wherein:
said first flow line branch is coupled to said second flow line branch at a first location,
said at least two injection fluid chambers are coupled to said first flow line branch at a second location, and
said borehole tool further comprises an isolation valve between said first and second locations.

16. A borehole tool according to claim 15, wherein:
said at least two injection fluid chambers are coupled to said first flow line branch at a third location, and
said borehole tool further comprises another isolation valve between said first and third locations.

17. A borehole tool according to claim 1, wherein:
said source probe comprises a hollow metal cylinder having a wall of a first thickness, said wall having a portion which tapers down in thickness at an end portion of said hollow metal cylinder which makes contact with said wall of said uncased borehole, said tapered portion of said wall having an elastomeric member thereabout.

18. A borehole tool according to claim 17, wherein:
said elastomeric member increases in thickness as said wall of said hollow metal cylinder decreases in thickness.

19. A method for making permeability measurements of a formation with a borehole tool, said borehole tool having a source probe which is in fluid contact with a wall of said borehole, a fluid flow line for bringing fluids to said source probe, at least two injection fluid chambers containing respectively clean oil and clean water, with said injection fluid chambers being in fluid contact with said fluid flow line, a plurality of valves for selectively routing said clean oil and clean water through said fluid flow line, and a pressure measurement means for measuring pressure resulting from the injection of said clean oil and the injection of said clean water into said formation, said method comprising:
a) injecting a first of said clean oil and the clean water into said formation, and measuring resulting pressure at said pressure measurement means;
b) cleaning said flow line with the other of said clean oil and said clean water;
c) injecting said other of said clean oil and said clean water into said formation, and measuring resulting pressure at said pressure measurement means.

20. A method according to claim 19, wherein:
said borehole contains water-based mud, and said clean water is injected first into said formation.

21. A method according to claim 19, wherein:
said borehole contains oil-based mud, and said oil is injected first into said formation.

22. A method according to claim 19, further comprising:
d) utilizing said pressure measurements to determine the endpoint relative water and oil permeabilities of said formation.

23. A method according to claim 19, wherein:
step a) comprises injecting between about 10 cc and 20 cc of fluid into said formation.

24. A method according to claim 19, wherein:
said borehole tool further comprises a pretest piston, and
step a) comprises using said pretest piston to inject said fluid into said formation.

25. A method according to claim 19, wherein:
said borehole tool further comprises a plurality of second valve means coupled between respective of said at least two injection fluid chambers and an uncased borehole in said formation, wherein when a particular said second valve means is open, borehole mud pressure bears on a respective said injection fluid chamber, and
step a) comprises opening a second valve means.

26. a method according to claim 19, further comprising:
d) utilizing said pressure measurements to determine the endpoint effective water and oil permeabilities of said formation.

27. A method according to claim 19, further comprising:
d) prior to step a), drawing formation fluid into said borehole tool.

28. A method according to claim 27, further comprising:
e) after step d), but prior to step a), cleaning said fluid flow line with one of said clean oil and said clean water.

29. A method according to claim 28, wherein:
said fluid flow line is cleaned with the same kind of fluid which is injected into said formation in step a).

30. A borehole tool according to claim 1, wherein:
said at least one injection fluid chamber comprises at least two injection fluid chambers, with a first of said at least two injection fluid chambers containing clean oil, and a second of said at least two injection fluid chambers containing clean water, wherein each of said at least two injection fluid chambers is in fluid communication with said fluid flow line.

31. A borehole tool according to claim 1, wherein:
said fluid flow line comprises at least a first flow line branch coupled to said at least one injection fluid chamber, and a second flow line branch coupled betwen said first flow line branch and said source probe, and said cleaning means comprises said first and second flow line branches and a plurality of valves which selectively route said one of said clean oil and clean water through said first and second flow line branches.

32. A borehole tool according to claim 30, wherein: said fluid flow line comprises at least a first flow line branch coupled to said at least two injection fluid chambers, and a second flow line branch coupled betwen said first flow line branch and said source probe, and said cleaning means comprises said first and second flow line branches and a plurality of valves which selectively route said clean oil and clean water through said first and second flow line branches.

* * * * *